United States Patent
Chen et al.

(10) Patent No.: US 11,952,596 B2
(45) Date of Patent: Apr. 9, 2024

(54) **APPLICATION OF GLUTAMATE DEHYDROGENASE GDHA OF *PEPTOSTREPTOCOCCUS ASACCHAROLYTICUS* IN INCREASING YIELD OF POLY-R-GLUTAMIC ACID FROM *BACILLUS LICHENIFORMIS***

(71) Applicant: Hubei University, Hubei (CN)

(72) Inventors: Shouwen Chen, Wuhan (CN); Fan Yang, Wuhan (CN); Dongbo Cai, Wuhan (CN); Yaozhong Chen, Wuhan (CN); Qing Zhang, Wuhan (CN); Xin Ma, Wuhan (CN); Jiangang Chen, Wuhan (CN)

(73) Assignee: Hubei University, Hubei (CN)

( * ) Notice: Subject to any disclaimer, the term of this patent is extended or adjusted under 35 U.S.C. 154(b) by 648 days.

(21) Appl. No.: 17/037,671

(22) Filed: Sep. 30, 2020

(65) Prior Publication Data
US 2021/0171918 A1    Jun. 10, 2021

(30) Foreign Application Priority Data
Dec. 5, 2019 (CN) .......................... 201911236047.7

(51) Int. Cl.
| | | |
|---|---|---|
| *C12N 9/06* | (2006.01) | |
| *C12N 1/20* | (2006.01) | |
| *C12P 13/02* | (2006.01) | |
| *C12R 1/10* | (2006.01) | |

(52) U.S. Cl.
CPC ........... *C12N 9/0016* (2013.01); *C12N 1/205* (2021.05); *C12P 13/02* (2013.01); *C12Y 104/01002* (2013.01); *C12Y 104/01003* (2013.01); *C12Y 104/01004* (2013.01); *C12R 2001/10* (2021.05)

(58) Field of Classification Search
CPC ........ C12N 9/0016; C12N 1/205; C12N 1/38; C12P 13/02; C12P 21/02; C12Y 104/01002; C12Y 104/01003; C12Y 104/01004
See application file for complete search history.

(56) References Cited

PUBLICATIONS

Tian et al. Glutamate dehydrogenase (RocG) in Bacillus licheniformis WX-02: enzymatic properties and specific functions in glutamate synthesis for poly-gamma-glutamic acid production. Enzyme and Microbial Technology (2017), 99: 9-15. (Year: 2017).*
Anonymous et al. Codon optimized genes. RD639061, publication Jul. 2017. (Year: 2017).*
J.B. Carrigan et al., "Probing the determinants of coenzyme specificity in Peptostreptococcus asaccharolyticus glutamate dehydrogenase by site-directed mutagenesis," Journal, No. 274, pp. 5167-5174 (2007).
Guangming Tian et al., "Glutamate dehydrogenase (RocG) in Bacillus licheniformis WX-02:Enzymatic properties and specific functions in glutamic acid synthesisfor poly-r-glutamic acid production," Enzyme and Microbial Technology, No. 99, pp. 9-15 (2017).

* cited by examiner

*Primary Examiner* — Iqbal H Chowdhury
(74) *Attorney, Agent, or Firm* — Mei & Mark LLP; Manni Li

(57) ABSTRACT

Application of glutamate dehydrogenase GdhA of *Peptostreptococcus asaccharolyticus* in increasing the yield of poly-γ-glutamic acid from *Bacillus licheniformis*. The glutamate dehydrogenase GdhA of the *Bacillus licheniformis* WX-02 per se is replaced with the glutamate dehydrogenase derived from the *Peptostreptococcus asaccharolyticus* by means of homologous recombination, which significantly increases the level of synthesizing the poly-γ-glutamic acid for the *Bacillus licheniformis*, and the yield of the obtained poly-γ-glutamic acid from strains is increased at least by more than 20% compared with control strains.

8 Claims, No Drawings
Specification includes a Sequence Listing.

APPLICATION OF GLUTAMATE DEHYDROGENASE GDHA OF *PEPTOSTREPTOCOCCUS ASACCHAROLYTICUS* IN INCREASING YIELD OF POLY-R-GLUTAMIC ACID FROM *BACILLUS LICHENIFORMIS*

CROSS-REFERENCE TO RELATED APPLICATIONS

The subject application claims priority on Chinese application no. 201911236047.7 filed on Dec. 5, 2019 in China. The contents and subject matters of the Chinese priority application is incorporated herein by reference.

BACKGROUND OF THE INVENTION

Technical Field

The invention belongs to the technical field of enzyme engineering and gene engineering, and in particular, relates to the application of glutamate dehydrogenase GdhA of *Peptostreptococcus asaccharolyticus* in increasing the yield of poly-γ-glutamic acid from *Bacillus licheniformis*.

Description of Related Art

Poly-γ-glutamic acid is an anionic polypeptide that is linked by an amide bond between an α-amino group and a γ-carboxylic acid group and is composed of D/L-type glutamic acid residues. The poly-γ-glutamic acid has numerous excellent properties due to its biological structural characteristics. As a water-soluble, biocompatible, edible, and non-toxic biodegradable material, the poly-γ-glutamic acid can be widely applied in fields such as food, agriculture, medicine, cosmetics, and environmental protection. Therefore, poly-γ-glutamic acid has a broad application prospect.

At present, the commercial production of poly-γ-glutamic acid mainly depends on microbiological fermentation. However, due to the need of adding precursors for synthesizing the poly-γ-glutamic acid and excessive fermentation by-products, the rate of conversion from glucose to the poly-γ-glutamic acid is low. It is currently reported that strains for commercially producing the poly-γ-glutamic acid are almost completely dependent on *Bacillus*, such as *Bacillus subtilis*, *Bacillus amyloliquefaciens*, and *Bacillus licheniformis*. Based on nutritional requirements, these strains for producing the poly-γ-glutamic acid can be divided into an L-glutamate-dependent type and an L-glutamate-independent type. The L-glutamate-dependent strains lead to an increase in the production cost of commercial production. Although the L-glutamate-independent strains are potentially low-cost cell factories, their productivity is greatly restricted. As a key enzyme in the pathway of synthesizing the poly-γ-glutamic acid, glutamate dehydrogenase is responsible for catalyzing α-ketoglutaric acid to form the glutamic acid, which then further reacts by a poly-γ-glutamate synthetase to produce a final product poly-γ-glutamic acid. Since the synthesis and accumulation of intracellular glutamic acid is an essential condition for the efficient synthesis of the poly-γ-glutamic acid, the glutamate dehydrogenase is also a key enzyme in the biosynthesis of the poly-γ-glutamic acid. At present, there is no study on the analysis and investigation of the glutamate dehydrogenase that affects the high yield of the poly-γ-glutamic acid. *Peptostreptococcus asaccharolyticus* is normal flora in the oral cavity, the upper respiratory tract, and the intestinal tract of a human body. There is neither study showing that the *Peptostreptococcus asaccharolyticus* has the capability of synthesizing the poly-γ-glutamic acid, nor study where the glutamate dehydrogenase has been investigated and compared with the glutamate dehydrogenase of the *Bacillus*.

BRIEF SUMMARY OF THE INVENTION

In the invention, the glutamate dehydrogenase of the *Bacillus licheniformis* per se is replaced with the glutamate dehydrogenase derived from the *Peptostreptococcus asaccharolyticus*, which significantly increases the level of synthesizing the poly-γ-glutamic acid from the *Bacillus licheniformis*, and achieve the technical effect of improving the yield of poly-γ-glutamic acid. The invention shows that the glutamate dehydrogenase in the *Peptostreptococcus asaccharolyticus* is of great significance for the efficient synthesis of the poly-γ-glutamic acid from the *Bacillus licheniformis*, and provides a new strategy for the efficient biosynthesis of the poly-γ-glutamic acid.

An object of the invention is to provide the application of glutamate dehydrogenase GdhA derived from *Peptostreptococcus asaccharolyticus* in increasing the yield of poly-γ-glutamic acid from *Bacillus licheniformis*, and an amino acid sequence of said glutamate dehydrogenase GdhA is as shown in SEQ ID NO:1.

To achieve the object described above, a technical measure employed in the invention is as follows.

The application of glutamate dehydrogenase GdhA of *Peptostreptococcus asaccharolyticus* in increasing the yield of poly-γ-glutamic acid from *Bacillus licheniformis* includes: replacing a glutamate dehydrogenase gene in *Bacillus licheniformis* with a gene encoding the glutamate dehydrogenase of the *Peptostreptococcus asaccharolyticus* to obtain a recombinant strain, which is then used for producing the poly-γ-glutamic acid through fermentation, wherein an amino acid sequence of the glutamate dehydrogenase gdhA is shown in SEQ ID NO: 1; or expressing the glutamate dehydrogenase GdhA of the *Peptostreptococcus asaccharolyticus* in the *Bacillus licheniformis* with a conventional solution in the art, thereby facilitating the synthesis of the poly-γ-glutamic acid.

In the above-mentioned application, preferably, a nucleotide sequence encoding the amino acid sequence shown in SEQ ID NO:1 is shown in SEQ ID NO:2.

In the above-mentioned application, preferably, the *Bacillus licheniformis* is *Bacillus licheniformis* capable of producing the poly-γ-glutamic acid.

In the above-mentioned application, preferably, the *Bacillus licheniformis* is *Bacillus licheniformis* WX-02.

In the above-mentioned application, the composition of fermentation media used during the fermentation in the application process is as follows:

30-90 g/L of glucose, 0-30 g/L of sodium glutamate, 0-10 g/L of sodium citrate, 5-10 g/L of $NaNO_3$, 0-10 g/L of $NH_4Cl$, 0.5-1 g/L of $K_2HPO_4 \cdot 3H_2O$, 0.8-1.2 g/L of $MgSO_4 \cdot 7H_2O$, 0.8-1.2 g/L of $ZnSO_4 \cdot 7H_2O$, 0.1-0.2 g/L of $MnSO_4 \cdot H_2O$, and 0.8-1.2 g/L of $CaCl_2$, wherein at most one of the sodium glutamate, the sodium citrate, and the ammonium chloride can be 0 in the content; or 18-22 g/L of glycerol, 25-35 g/L of sodium glutamate, 8-13 g/L of sodium citrate, 7-12 g/L of $NaNO_3$, 8-12 g/L of $NH_4Cl$, 0.8-1.2 g/L of $K_2HPO_4 \cdot 3H_2O$, 0.9-1.2 g/L of $MgSO_4 \cdot 7H_2O$, 0.8-1.2 g/L of $ZnSO_4 \cdot 7H_2O$, 0.1-0.25 g/L of $MnSO_4 \cdot H_2O$, and 0.5-1.5 g/L of $CaCl_2$.

In the above-mentioned application, the composition of the fermentation media used during the fermentation in the application process is as follows:

30-90 g/L of glucose, 0-30 g/L of sodium glutamate, 9-10 g/L of sodium citrate, 9-10 g/L of NaNO$_3$, 9-10 g/L of NH$_4$Cl, 0.8-1 g/L of K$_2$HPO$_4$·3H$_2$O, 0.8-1 g/L of MgSO$_4$·7H$_2$O, 0.8-1 g/L of ZnSO$_4$·7H$_2$O, 0.1-0.2 g/L of MnSO$_4$·H$_2$O, and 0.8-1.2 g/L of CaCl$_2$, wherein the sodium glutamate and the sodium citrate cannot be 0 in content at the same time.

Compared with the prior art, the invention has the following advantages.

The invention replaced the glutamate dehydrogenase GdhA of the *Bacillus licheniformis* WX-02 per se with the glutamate dehydrogenase GdhA derived from the *Peptostreptococcus asaccharolyticus* by means of homologous recombination, which solves the problem of short supply of the glutamic acid in the current synthesis process of the poly-γ-glutamic acid. The modified strains are significantly enhanced in the synthesis capability of the poly-γ-glutamic acid, and is at least increased by 20% in the level of synthesizing the poly-γ-glutamic acid as compared with control strains.

DETAILED DESCRIPTION OF THE INVENTION

Embodiments below are intended to further explain rather than limiting the invention. The technical solutions of the invention are conventional solutions in the art unless otherwise specified. The reagents or materials described are commercially available unless otherwise specified.

Experiment Materials and Reagents

1. Strains: *Bacillus licheniformis* WX-02, with the Accession No. of CCTCC NO. M208065. The deposit of the biological material was made at China Center for Type Culture Collection (CCTCC), having an address at Wuhan University, Luojiashan, Wuchang, Wuhan, 430072, China, on Apr. 28, 2008; the deposit has the CCTCC Accession No. M208065; the deposited biological material is described as *Bacillus licheniformis* WX-02; and the deposit has been made under the Budapest Treaty.

The strains *E. coli* DH5a are commercially available and purchased from Beijing TransGen Biotech Co., Ltd.

2. Enzymes and other biochemical reagents: High-fidelity Taq enzyme was purchased from Wuhan Qingke Biotechnology Co., Ltd. Bacterial genomic DNA extraction kit was purchased from Tiangen; T4 DNA ligases, restriction endonucleases, and other molecular biological reagents were purchased from Nanjing Vazyme Biotech Co., Ltd; and others were domestic reagents (all available from ordinary biochemical reagent companies).

3. Media:

Composition of LB media includes: 10 g/L of tryptone, 5 g/L of yeast powder, 10 g/L of sodium chloride; and the LB media had a pH of 7.0-7.2 and were sterilized at 121° C. for 20 min before use.

Example 1. Construction of Replacement of Strain *Bacillus licheniformis* WX-gdhA with Glutamate Dehydrogenase of *Peptostreptococcus asaccharolyticus*

(1) a gdhA gene (as shown in SEQ ID NO: 2) is synthesized according to genomic DNA sequence of *Peptostreptococcus asaccharolyticus* DSM 20463 (GenBank Access No. NZ_FWWR00000000.1), wherein primers for amplifying the gene included T2-F2 of SEQ ID NO: 3 and T2-R2 SEQ ID NO: 4; and an upstream homologous arm (T2-F1 SEQ ID NO: 5 and T2-R1 SEQ ID NO: 6 as primers) and a downstream homologous arm (T2-F3 SEQ ID NO: 7 and T2-R3 SEQ ID NO: 8 as primers) of a glutamate dehydrogenase gene rocG (GenBank Access NO. AKQ74236.1) of the *Bacillus licheniformis* per se are amplified through PCR with the genomic DNA of the *Bacillus licheniformis* WX-02 (GenBank Access No. NZ_CP012110.1) as a template;

```
                                    (SEQ ID NO: 5)
T2-F1: GGGAGCTCTGCTGTAGTATTGCTGGCC;

(SEQ ID NO: 6)
T2-R1: ATTAAGTGTATCTGTCATCTTTTTTCAGCTCCCTTTCT;

(SEQ ID NO: 3)
T2-F2: AGAAAGGGAGCTGAAAAAAGATGACAGATACACTTAAT;

(SEQ ID NO: 4)
T2-R2: ATGCTCTCTCTTTTTACCGTTAATACCATCCTCTTAATT;

(SEQ ID NO: 7)
T2-F3: AATTAAGAGGATGGTATTAACGGTAAAAAGAGAGAGCAT;

(SEQ ID NO: 8)
T2-R3: GCTCTAGAATTTTGATTAATCAATCTAC;
```

(2) the upstream homologous arm of the gene rocG (SEQ ID NO: 13), the amplified gdhA gene and the downstream homologous arm of the gene rocG (SEQ ID NO: 14) are linked through overlap-extension PCR to form a target gene fragment, which has an order as follows: the upstream homologous arm of the gene rocG—the amplified gdhA gene—the downstream homologous arm of the gene rocG;

(3) double digestion is performed on the target gene fragment using restriction endonucleases SacI and XbaI to obtain digested gene fragments, and meanwhile, double digestion is performed on a plasmid T2(2)-Ori using the restriction endonucleases SacI and XbaI to obtain linear plasmid fragments;

(4) the digested target fragments obtained in step (3) is linked with the linear plasmid fragments obtained in step (3) via T4-DNA ligases, and the correctness is verified to obtain plasmids T2(2)-gdhA;

(5) the plasmids T2(2)-gdhA are transferred into the *Bacillus licheniformis* WX-02, and screened by media resistant to kanacillin to obtain transformants, and the plasmids are picked from the transformants for colony PCR verification;

(6) positive transformants obtained in step (4) are transferred to cultured on the media resistant to kanacillin at 45° C. 3 times, each for 12 hours, and colony PCR is performed to detect single-exchange strains with T2-KYF and gdhA-R as primers;

```
                                    (SEQ ID NO: 9)
T2-KYF: TCAACAGCCTCTACAATAAA;
and
                                    (SEQ ID NO: 10)
gdhA-R: TTAATACCATCCTCTTAATT;
```

(7) strains obtained in step (5) and the single-exchange strains obtained in step (6) are mixed and inoculated, and then transferred to and cultured in media containing no kanacillin at 37° C. several times; the transformants are picked for colony PCR verification to obtain positive transformants; and DNA sequencing is performed on the positive transformants for further verification, thereby obtaining successfully double-exchanged recombinant strains. Then, the positive transformants are obtained. Subsequently, DNA sequencing is performed on the positive transformants for further verification, and successfully double-exchanged gdhA strains (i.e., *Bacillus licheniformis* WX-gdhA) is obtained.

```
                                   (SEQ ID NO: 11)
T2-KYF: TCAACAGCCTCTACAATAAA;
and
                                   (SEQ ID NO: 12)
T2-KYR: ATGAACGCTTTAAACGAT.
```

Example 2. Application of *Bacillus licheniformis* WX-gdhA in Increasing the Fermentation Yield of Poly-γ-Glutamic Acid Analysis of Yield of Fermentation Product The recombinant strains obtained in Example 1 is inoculated into the LB media and cultured at 37° C. for 14 h; 50 mL of poly-γ-glutamic acid fermentation medium (Table 1) is put into a 500 mL Erlenmeyer flask, and then a seed-culturing bacteria liquid is inoculated into the fermentation media at an inoculum amount of 3% (volume percentage). The culture is performed at the speed of 230 r/min and at the temperature of 37° C. for a fermentation period of 36 hours.

In this example, the effect of the *Bacillus licheniformis* WX-gdhA on the synthesis level of the poly-γ-glutamic acid is investigated with respect to different compositions of the fermentation media (at the same time, these 24 media were inoculated with the same inoculation amount of *Bacillus licheniformis* WX-02 as controls). The specific compositions of the 24 media are shown in Table 1:

TABLE 1

Compositions of fermentation media

| Media Composition No. | Glucose | Glycerol | Na glutamate | Na Citrate | NaNO$_3$ | NH$_4$Cl | K$_2$HPO$_4$·3H$_2$O | MgSO$_4$·7H$_2$O | ZnSO$_4$·7H$_2$O | MnSO$_4$·H$_2$O | CaCl$_2$ |
|---|---|---|---|---|---|---|---|---|---|---|---|
| 1  | 90 | 0  | 30 | 10 | 10 | 10 | 1   | 1   | 1   | 0.15  | 1   |
| 2  | 60 | 0  | 30 | 10 | 10 | 10 | 1   | 1   | 1   | 0.15  | 1   |
| 3  | 30 | 0  | 30 | 10 | 10 | 10 | 1   | 1   | 1   | 0.15  | 1   |
| 4  | 90 | 0  | 15 | 10 | 10 | 10 | 1   | 1   | 1   | 0.15  | 1   |
| 5  | 90 | 0  | 0  | 10 | 10 | 10 | 1   | 1   | 1   | 0.15  | 1   |
| 6  | 90 | 0  | 30 | 5  | 10 | 10 | 1   | 1   | 1   | 0.15  | 1   |
| 7  | 90 | 0  | 30 | 0  | 10 | 10 | 1   | 1   | 1   | 0.15  | 1   |
| 8  | 90 | 0  | 30 | 10 | 5  | 10 | 1   | 1   | 1   | 0.15  | 1   |
| 9  | 90 | 0  | 30 | 10 | 0  | 10 | 1   | 1   | 1   | 0.15  | 1   |
| 10 | 90 | 0  | 30 | 10 | 10 | 5  | 1   | 1   | 1   | 0.15  | 1   |
| 11 | 90 | 0  | 30 | 10 | 10 | 0  | 1   | 1   | 1   | 0.15  | 1   |
| 12 | 90 | 0  | 30 | 10 | 10 | 10 | 0.5 | 1   | 1   | 0.15  | 1   |
| 13 | 90 | 0  | 30 | 10 | 10 | 10 | 0   | 1   | 1   | 0.15  | 1   |
| 14 | 90 | 0  | 30 | 10 | 10 | 10 | 1   | 0.5 | 1   | 0.15  | 1   |
| 15 | 90 | 0  | 30 | 10 | 10 | 10 | 1   | 0   | 1   | 0.15  | 1   |
| 16 | 90 | 0  | 30 | 10 | 10 | 10 | 1   | 1   | 0.5 | 0.15  | 1   |
| 17 | 90 | 0  | 30 | 10 | 10 | 10 | 1   | 1   | 0   | 0.15  | 1   |
| 18 | 90 | 0  | 30 | 10 | 10 | 10 | 1   | 1   | 1   | 0.075 | 1   |
| 19 | 90 | 0  | 30 | 10 | 10 | 10 | 1   | 1   | 1   | 0     | 1   |
| 20 | 90 | 0  | 30 | 10 | 10 | 10 | 1   | 1   | 1   | 0.15  | 0.5 |
| 21 | 90 | 0  | 30 | 10 | 10 | 10 | 1   | 1   | 1   | 0.15  | 0   |
| 22 | 0  | 20 | 30 | 10 | 10 | 10 | 1   | 1   | 1   | 0.15  | 1   |
| 23 | 0  | 40 | 30 | 10 | 10 | 10 | 1   | 1   | 1   | 0.15  | 1   |
| 24 | 0  | 60 | 30 | 10 | 10 | 10 | 1   | 1   | 1   | 0.15  | 1   |

The media compositions above are all in g/L, and the fermentation media have the pH of 6.5-7.2 and are sterilized at 115° C. for 20 min before use.

The yield of the poly-γ-glutamic acid is measured by a dry weight method, with the specific operation steps as follows. A certain volume of fermentation broth sample is taken, adjusted to 3.0 in pH with 6 mol/L HCl and centrifuged at 12000 r/min for 10 min; bacterial precipitates are dried in an oven at 80° C.; the dry weight of the bacteria is measured.

A supernatant is taken, adjusted to neutrality in pH with 6 mol/L NaOH, added with ethanol to precipitate the poly-γ-glutamic acid, wherein the volume of the ethanol is 3 times that of the supernatant; a resultant product is centrifuged to collect flocculent precipitates of the poly-γ-glutamic acid, and the precipitates are dried in the oven at 80° C. and measured in dry weight. The yield of the poly-γ-glutamic acid in the fermentation broth is calculated according to the dry weight method (see Table 2).

TABLE 2

Yields of poly-γ-glutamic acid in fermentation test

| Media Composition No. | The yield of poly-γ-glutamic acid from strains WX-rocGS$^{277W}$ (g/L) | The yield of poly-γ-glutamic acid from control strains WX-02 (g/L) | Increase percentage in yield of poly-γ-glutamic acid (%) |
|---|---|---|---|
| 1 | 44.67 | 35.35 | 26.36 |
| 2 | 38.36 | 30.25 | 26.81 |
| 3 | 30.14 | 22.45 | 34.25 |
| 4 | 33.73 | 25.25 | 33.58 |
| 5 | 22.77 | 16.75 | 35.94 |
| 6 | 34.77 | 28.48 | 22.09 |
| 7 | 28.45 | 20.55 | 38.44 |
| 8 | 32.53 | 24.26 | 34.09 |
| 9 | 25.34 | 19.12 | 32.53 |
| 10 | 35.25 | 27.87 | 26.48 |
| 11 | 34.86 | 27.64 | 26.12 |
| 12 | 38.77 | 30.45 | 27.32 |
| 13 | 36.81 | 30.65 | 20.10 |
| 14 | 34.03 | 27.98 | 21.62 |
| 15 | 32.68 | 25.47 | 28.31 |
| 16 | 36.17 | 29.44 | 22.86 |
| 17 | 34.75 | 27.68 | 25.54 |
| 18 | 31.13 | 24.82 | 25.42 |
| 19 | 24.52 | 20.36 | 20.43 |
| 20 | 33.77 | 27.45 | 23.02 |
| 21 | 30.87 | 25.08 | 23.09 |
| 22 | 26.14 | 19.99 | 30.77 |
| 23 | 31.85 | 25.54 | 24.71 |
| 24 | 36.88 | 30.17 | 22.24 |

The invention provides a new strategy for the efficient production of poly-γ-glutamic acid.

We claim:

1. A method for increasing yield of poly-γ-glutamic acid produced by *Bacillus licheniformis* through fermentation, comprising:

replacing a glutamate dehydrogenase gene in *Bacillus licheniformis* with a glutamate dehydrogenase gene (gdhA) of *Peptostreptococcus asaccharolyticus* to obtain a recombinant strain, producing the poly-γ-glutamic acid through fermentation of the recombinant strain.

2. The method according to claim 1, wherein the *Bacillus licheniformis* is *Bacillus licheniformis* WX-02 with CCTCC Accession No. M208065.

3. The method according to claim 1, wherein the glutamate dehydrogenase gene of the *Peptostreptococcus asaccharolyticus* is as shown in SEQ ID NO:2.

4. The method according to claim 1, wherein fermentation media used during the fermentation comprise:

30-90 g/L of glucose, 0-30 g/L of sodium glutamate, 0-10 g/L of sodium citrate, 5-10 g/L of NaNO$_3$, 0-10 g/L of NH$_4$Cl, 0.5-1 g/L of K$_2$HPO$_4$·3H$_2$O, 0.8-1.2 g/L of MgSO$_4$·7H$_2$O, 0.8-1.2 g/L of ZnSO$_4$·7H$_2$O, 0.1-0.2 g/L of MnSO$_4$·H$_2$O, and 0.8-1.2 g/L of CaCl$_2$), wherein at most one of the sodium glutamate, the sodium citrate, and the ammonium chloride is optionally 0 in the content; or 18-22 g/L of glycerol, 25-35 g/L of sodium glutamate, 8-13 g/L of sodium citrate, 7-12 g/L of NaNO$_3$, 8-12 g/L of NH$_4$Cl, 0.8-1.2 g/L of K$_2$HPO$_4$·3H$_2$O, 0.9-1.2 g/L of MgSO$_4$·7H$_2$O, 0.8-1.2 g/L of ZnSO$_4$·7H$_2$O, 0.1-0.25 g/L of MnSO$_4$·H$_2$O, and 0.5-1.5 g/L of CaCl$_2$.

5. The method according to claim 4, wherein the fermentation media used during fermentation comprise:

30-90 g/L of glucose, 0-30 g/L of sodium glutamate, 9-10 g/L of sodium citrate, 9-10 g/L of NaNO$_3$, 9-10 g/L of NH$_4$Cl, 0.8-1 g/L of K$_2$HPO$_4$·3H$_2$O, 0.8-1 g/L of MgSO$_4$·7H$_2$O, 0.8-1 g/L of ZnSO$_4$·7H$_2$O, 0.1-0.2 g/L of MnSO$_4$·H$_2$O, and 0.8-1.2 g/L of CaCl$_2$, and the sodium glutamate and the sodium citrate are not 0 in content at same time.

6. The method according to claim 3, wherein a protein encoded by the glutamate dehydrogenase gene of the *Peptostreptococcus asaccharolyticus* is as shown in SEQ ID NO:1.

7. The method according to claim 1, wherein the recombinant strain is obtained by the following steps of
   (1) synthesizing the glutamate dehydrogenase gene (gdhA) according to a genomic DNA sequence of *Peptostreptococcus asaccharolyticus* DSM 20463 to obtain a synthesized gdhA gene, wherein the synthesized gdhA gene has a sequence shown in SEQ ID NO:2, and primers for amplifying the gdhA gene comprise T2-F2 of SEQ ID NO:3 and T2-R2 of SEQ ID NO:4,
   amplifying an upstream homologous arm and a downstream homologous arm of a glutamate dehydrogenase gene (rocG) of the *Bacillus licheniformis* per se through PCR with a genomic DNA of *Bacillus licheniformis* WX-02 as a template, wherein primers for amplifying the upstream homologous arm comprise T2-F1 of SEQ ID NO: 5 and T2-R1 of SEQ ID NO: 6; and primers for amplifying the downstream homologous arm comprise T2-F3 of SEQ ID NO: 7 and T2-R3 of SEQ ID NO: 8;
   (2) linking the upstream homologous arm of the rocG gene, the amplified gdhA gene, and the downstream homologous arm of the rocG gene through overlap-extension PCR to form a target gene fragment in an order of the upstream homologous arm of the gene rocG—the amplified gdhA gene—the downstream homologous arm of the gene rocG;
   (3) performing double digestion on the target gene fragment using restriction endonucleases SacI and XbaI to obtain digested target gene fragments, and meanwhile, performing double digestion on a plasmid T2(2)-Ori using the restriction endonucleases SacI and XbaI to obtain linear plasmid fragments;
   (4) linking the digested target fragments obtained in step (3) with the linear plasmid fragments obtained in step (3) via T4-DNA ligases, and verifying correctness to obtain plasmids T2(2)-gdhA;
   (5) transferring the plasmids T2(2)-gdhA into the *Bacillus licheniformis* WX-02 to obtain transformants and picking plasmids from the transformants for colony PCR verification to obtain verified strains;
   (6) transferring and culturing the transformants obtained in step (5) and performing colony PCR to detect single-exchange strains using T2-KYF of SEQ ID NO: 9 and gdhA-R of SEQ ID NO: 10 as primers; and
   (7) inoculating, mixing, and culturing the verified strains obtained in step (5) and the single-exchange strains obtained in step (6) to obtain mixed strains, transferring and culturing the mixed strains and picking transformants in the mixed strains for colony PCR verification to obtain positive transformants, and performing DNA sequencing on the positive transform ants for further verification, thereby obtaining successfully double-exchanged recombinant strains, wherein primers for the colony PCR verification are T2-KYF of SEQ ID NO: 11 and T2-KYR of SEQ ID NO: 12.

8. The method according to claim 4, wherein conditions for the fermentation comprise inoculating a bacterial liquid of the recombinant strains into the fermentation media at an inoculation amount of 3% by volume, and culturing at the speed of 230 r/min and at the temperature of 37° C. for a fermentation period of 36 hours.

\* \* \* \* \*

SEQUENCE LISTING

<160> NUMBER OF SEQ ID NOS: 14

<210> SEQ ID NO 1
<211> LENGTH: 421
<212> TYPE: PRT
<213> ORGANISM: Peptostreptococcus asaccharolyticus

<400> SEQUENCE: 1

```
Met Thr Asp Thr Leu Asn Pro Leu Val Ala Ala Gln Glu Lys Val Arg
1               5                   10                  15

Ile Ala Cys Glu Lys Leu Gly Cys Asp Pro Ala Val Tyr Glu Leu Leu
            20                  25                  30

Lys Glu Pro Gln Arg Val Ile Glu Ile Ser Ile Pro Val Lys Met Asp
        35                  40                  45

Asp Gly Thr Val Lys Val Phe Lys Gly Trp Arg Ser Ala His Ser Ser
    50                  55                  60

Ala Val Gly Pro Ser Lys Gly Val Arg Phe His Pro Asn Val Asn
65                  70                  75                  80

Met Asp Glu Val Lys Ala Leu Ser Leu Trp Met Thr Phe Lys Gly Gly
            85                  90                  95
```

Ala Leu Gly Leu Pro Tyr Gly Gly Lys Gly Ile Cys Val Asp
            100                 105                 110

Pro Ala Glu Leu Ser Glu Arg Glu Leu Glu Gln Leu Ser Arg Gly Trp
            115                 120                 125

Val Arg Gly Leu Tyr Lys Tyr Leu Gly Asp Arg Ile Asp Ile Pro Ala
            130                 135                 140

Pro Asp Val Asn Thr Asn Gly Gln Ile Met Ser Trp Phe Val Asp Glu
145                 150                 155                 160

Tyr Val Lys Leu Asn Gly Glu Arg Met Asp Ile Gly Thr Phe Thr Gly
            165                 170                 175

Lys Pro Val Ala Phe Gly Gly Ser Glu Gly Arg Asn Glu Ala Thr Gly
            180                 185                 190

Phe Gly Val Ala Val Val Arg Glu Ser Ala Lys Arg Phe Gly Ile
            195                 200                 205

Lys Met Glu Asp Ala Lys Ile Ala Val Gln Gly Phe Gly Asn Val Gly
            210                 215                 220

Thr Phe Thr Val Lys Asn Ile Glu Arg Gln Gly Gly Lys Val Cys Ala
225                 230                 235                 240

Ile Ala Glu Trp Asp Arg Asn Glu Gly Asn Tyr Ala Leu Tyr Asn Glu
            245                 250                 255

Asn Gly Ile Asp Phe Lys Glu Leu Leu Ala Tyr Lys Glu Ala Asn Lys
            260                 265                 270

Thr Leu Ile Gly Phe Pro Gly Ala Glu Arg Ile Thr Asp Glu Glu Phe
            275                 280                 285

Trp Thr Lys Glu Tyr Asp Ile Ile Val Pro Ala Ala Leu Glu Asn Val
            290                 295                 300

Ile Thr Gly Glu Arg Ala Lys Thr Ile Asn Ala Lys Leu Val Cys Glu
305                 310                 315                 320

Ala Ala Asn Gly Pro Thr Thr Pro Glu Gly Asp Lys Val Leu Thr Glu
            325                 330                 335

Arg Gly Ile Asn Leu Thr Pro Asp Ile Leu Thr Asn Ser Gly Gly Val
            340                 345                 350

Leu Val Ser Tyr Tyr Glu Trp Val Gln Asn Gln Tyr Gly Tyr Tyr Trp
            355                 360                 365

Thr Glu Ala Glu Val Glu Glu Lys Gln Glu Ala Asp Met Met Lys Ala
            370                 375                 380

Ile Lys Gly Val Phe Ala Val Ala Asp Glu Tyr Asn Val Thr Leu Arg
385                 390                 395                 400

Glu Ala Val Tyr Met Tyr Ala Ile Lys Ser Ile Asp Val Ala Met Lys
            405                 410                 415

Leu Arg Gly Trp Tyr
            420

<210> SEQ ID NO 2
<211> LENGTH: 1266
<212> TYPE: DNA
<213> ORGANISM: Peptostreptococcus asaccharolyticus

<400> SEQUENCE: 2
atgacagata cacttaatcc gttagtagcg gcacaagaaa aagtaagaat agcatgcgaa        60
aaattaggat gcgatccagc agtatatgaa ctattaaaag aaccacaaag agtaattgaa       120
atctcaattc cagtaaaaat ggatgatggt acagttaaag tgttcaaagg atggagaagt       180
gctcactcaa gcgctgtagg tccatcaaaa ggtggagtta gattccatcc aaatgtaaac       240

```
atggatgaag ttaaagctct ttctctatgg atgacattca aaggtggagc actaggctta    300
ccatacggcg gaggaaaagg tggaatctgc gtagatccag cagaactatc agaaagagaa    360
ttagaacaat tatcaagagg atgggtaaga ggtctttata aatatcttgg agacagaatc    420
gatatcccag caccagacgt aaacactaac ggacaaatca tgagctggtt cgttgatgaa    480
tatgtaaaat taaacggcga agaatggac  atcggaactt tcacaggaaa gccagtagca    540
tttggcggaa gtgaaggaag aaacgaagca actggattcg gagtagctgt agtagttaga    600
gaatctgcta agagattcgg aatcaaaatg gaagatgcta aaatagctgt tcaaggtttc    660
ggaaacgtag gtactttcac tgttaagaac attgaaagac aaggcggaaa agtttgtgct    720
atcgctgaat gggatagaaa cgaaggaaac tatgctctat acaatgaaaa tggaatcgac    780
ttcaaagaat tattagctta caagaagct  aacaaaactc ttatcggatt cccaggagca    840
gaaagaatta ctgatgaaga attctggaca aaagaatatg atatcatagt accagcagca    900
ttagaaaatg taatcacagg cgaaagagct aaaacaataa acgctaaatt agtttgtgaa    960
gcagctaatg gtcctacaac tccagaagga gacaaagtat taactgaaag aggaatcaac   1020
ttaacaccag atatcttaac taactcaggt ggagttctag tatcttacta tgaatgggta   1080
caaaatcaat atggatacta ctggacagaa gcagaagtag aagaaaaaca agaagcagac   1140
atgatgaaag ctatcaaagg cgtattcgca gttgctgatg aatacaatgt aactctaaga   1200
gaagctgttt acatgtatgc aatcaaatca atagatgtag ctatgaaatt aagaggatgg   1260
tattaa                                                              1266
```

<210> SEQ ID NO 3
<211> LENGTH: 38
<212> TYPE: DNA
<213> ORGANISM: Artificial Sequence
<220> FEATURE:
<223> OTHER INFORMATION: PCR Primer T2-F2

<400> SEQUENCE: 3
agaaagggag ctgaaaaaag atgacagata cacttaat                              38

<210> SEQ ID NO 4
<211> LENGTH: 39
<212> TYPE: DNA
<213> ORGANISM: Artificial Sequence
<220> FEATURE:
<223> OTHER INFORMATION: PCR Primer T2-R2

<400> SEQUENCE: 4
atgctctctc ttttaccgt taataccatc ctcttaatt                             39

<210> SEQ ID NO 5
<211> LENGTH: 27
<212> TYPE: DNA
<213> ORGANISM: Artificial Sequence
<220> FEATURE:
<223> OTHER INFORMATION: PCR Primer T2-F1

<400> SEQUENCE: 5
gggagctctg ctgtagtatt gctggcc                                         27

<210> SEQ ID NO 6
<211> LENGTH: 38
<212> TYPE: DNA
<213> ORGANISM: Artificial Sequence
<220> FEATURE:

```
<223> OTHER INFORMATION: PCR Primer T2-R1

<400> SEQUENCE: 6
attaagtgta tctgtcatct tttttcagct ccctttct                                38

<210> SEQ ID NO 7
<211> LENGTH: 39
<212> TYPE: DNA
<213> ORGANISM: Artificial Sequence
<220> FEATURE:
<223> OTHER INFORMATION: PCR Primer T2-F3

<400> SEQUENCE: 7
aattaagagg atggtattaa cggtaaaaag agagagcat                               39

<210> SEQ ID NO 8
<211> LENGTH: 28
<212> TYPE: DNA
<213> ORGANISM: Artificial Sequence
<220> FEATURE:
<223> OTHER INFORMATION: PCR Primer T2-R3

<400> SEQUENCE: 8
gctctagaat tttgattaat caatctac                                           28

<210> SEQ ID NO 9
<211> LENGTH: 20
<212> TYPE: DNA
<213> ORGANISM: Artificial Sequence
<220> FEATURE:
<223> OTHER INFORMATION: PCR Primer T2-KYF

<400> SEQUENCE: 9
tcaacagcct ctacaataaa                                                    20

<210> SEQ ID NO 10
<211> LENGTH: 20
<212> TYPE: DNA
<213> ORGANISM: Artificial Sequence
<220> FEATURE:
<223> OTHER INFORMATION: PCR Primer gdhA-R

<400> SEQUENCE: 10
ttaataccat cctcttaatt                                                    20

<210> SEQ ID NO 11
<211> LENGTH: 20
<212> TYPE: DNA
<213> ORGANISM: Artificial Sequence
<220> FEATURE:
<223> OTHER INFORMATION: PCR Primer T2-KYF

<400> SEQUENCE: 11
tcaacagcct ctacaataaa                                                    20

<210> SEQ ID NO 12
<211> LENGTH: 18
<212> TYPE: DNA
<213> ORGANISM: Artificial Sequence
<220> FEATURE:
<223> OTHER INFORMATION: PCR Primer T2-KYR

<400> SEQUENCE: 12
atgaacgctt taaacgat                                                      18
```

<210> SEQ ID NO 13
<211> LENGTH: 569
<212> TYPE: DNA
<213> ORGANISM: Bacillus licheniformis

<400> SEQUENCE: 13

```
tgctgtagta ttgctggcct tccttccatg gcgtgctttt gttctcaacg ggctcgtctt      60
tgccctgtgc agctccatac gcaccttcag gaaattcttc agctgttaaa aagtttcttt     120
gcgtttcaac gttcgacatt tcttttttgt cgtccatcag atcaccctg ttttagtttt      180
attgttgcca tgaaaaaggg gagctatgtg ttttcgtttt gtatgcagta ggtttcattt     240
taaaaacggg ataagatgct cattctctgc cgggagtaca aggggggaaa tgcgccgatc     300
acaaagaaaa tagacatttt gtacagaaag aacctgtcag ataaagtggt attttatggt    360
ttattggtcc ttttctcctc agcttttaag agctgtcctt ctatcttatg acccgtctat    420
tctcgctttt tgttatacat ctcaattcag caatggtttt atctgttttc cagattgatg    480
taaatggggc attggttgta aaatttacca tgagagaaaa tcttacaatg ttcgttctgc    540
ttttatttta gaaagggagc tgaaaaaag                                       569
```

<210> SEQ ID NO 14
<211> LENGTH: 539
<212> TYPE: DNA
<213> ORGANISM: Bacillus licheniformis

<400> SEQUENCE: 14

```
cggtaaaaag agagagcatg atgccctctc ttttttttgtg ctttattcat tgtctctgaa     60
tccaccggta aaggcgtgta cagccggaac ggaaattccc gggtagccga tgccgaatcc    120
gagcgtcgga gtggtgaaca ccccgccgta cggataatag gtatatggcc cgtgtgctga   180
aggattatag acataagtaa ccgggtagcc gaagtatccc gggtattggc gcacgcgggg   240
aacagagtgc gcaggaaaag tgcggtacat catattcacc tgtttctttt ttgattaaca   300
ccagtttatg taaaaaaatc gtaaaatgga gtctgtacat atatgtggca aaaaatctaa   360
ccggcgggga tgaaagtata aaaaattgtc gggataaaat ctaacaaaac tgtataaaac    420
gccagttttt ttatgtaatc tttatagatt acataaaaaa ttttaaattg ttttttcaatt    480
ttacatttcc tttatatca atcatgtaag cgtatacaag tagattgatt aatcaaaat     539
```